United States Patent
Okamoto et al.

(10) Patent No.: US 9,763,564 B2
(45) Date of Patent: Sep. 19, 2017

(54) INTRODUCING APPARATUS

(71) Applicant: OLYMPUS CORPORATION, Tokyo (JP)

(72) Inventors: Yasuhiro Okamoto, Hachioji (JP); Keijiro Omoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/990,087

(22) Filed: Jan. 7, 2016

(65) Prior Publication Data

US 2016/0113481 A1 Apr. 28, 2016

Related U.S. Application Data

(63) Continuation of application No. PCT/JP2014/066351, filed on Jun. 19, 2014.

(30) Foreign Application Priority Data

Jul. 8, 2013 (JP) ................. 2013-142539

(51) Int. Cl.
*A61B 1/005* (2006.01)
*A61B 1/00* (2006.01)

(52) U.S. Cl.
CPC .......... *A61B 1/0052* (2013.01); *A61B 1/0016* (2013.01); *A61B 1/00112* (2013.01); *A61B 1/00158* (2013.01)

(58) Field of Classification Search
CPC . A61B 1/0052; A61B 1/0016; A61B 1/00112; A61B 1/00158; A61B 1/00066
USPC ......................... 600/146–150, 132
See application file for complete search history.

(56) References Cited

U.S. PATENT DOCUMENTS

| | | | |
|---|---|---|---|
| 2005/0054898 A1 | 3/2005 | Moriyama | |
| 2012/0302829 A1* | 11/2012 | Omoto | A61B 1/0052 600/109 |
| 2015/0208902 A1 | 7/2015 | Okamoto | |

FOREIGN PATENT DOCUMENTS

| | | |
|---|---|---|
| CN | 105007797 A | 10/2015 |
| DE | 39 43 726 C2 | 1/1995 |
| EP | 1 757 217 A1 | 2/2007 |
| EP | 2 583 616 A1 | 4/2013 |
| EP | 3 011 890 A1 | 4/2016 |
| JP | S59-197229 A | 11/1984 |
| JP | H06-169889 A | 6/1994 |
| JP | H09-294718 A | 11/1997 |
| JP | 2004-008342 A | 1/2004 |

(Continued)

OTHER PUBLICATIONS

English translation of International Preliminary Report on Patentability dated Jan. 21, 2016 together with the Written Opinion received in related International Application No. PCT/JP2014/066351.

(Continued)

*Primary Examiner* — Timothy J Neal
(74) *Attorney, Agent, or Firm* — Scully, Scott, Murphy & Presser, P.C.

(57) ABSTRACT

The introducing apparatus comprises the operating section, which is easy to grip and easy to operate, mounted therein by providing the dial of the operation element to perform a bending operation of the bending section and a part of the rotary mechanism alone while avoiding an operation range of the operating section for fingers of a gripping hand.

8 Claims, 11 Drawing Sheets

(56) References Cited

FOREIGN PATENT DOCUMENTS

| JP | 2004-321492 A | 11/2004 |
| JP | 2005-160789 A | 6/2005 |
| WO | WO 2012/063880 A1 | 5/2012 |
| WO | WO 2012/074013 A1 | 6/2012 |
| WO | WO 2012/172953 A1 | 12/2012 |

OTHER PUBLICATIONS

Japanese Office Action dated Jun. 16, 2015 issued in JP 2015-511821.
International Search Report dated Sep. 16, 2014 issued in PCT/JP2014/066351.
Extended Supplementary European Search Report dated Mar. 8, 2017 in European Patent Application No. 14 82 22201.
Chinese Office Action dated Mar. 29, 2017 in Chinese Patent Application No. 201480038724.3.

\* cited by examiner

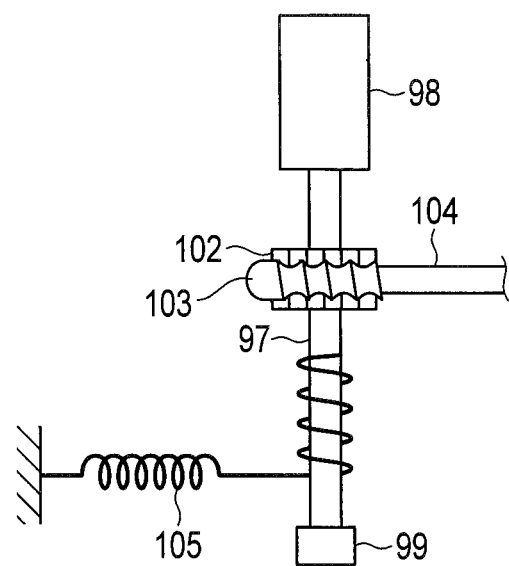
F I G. 17
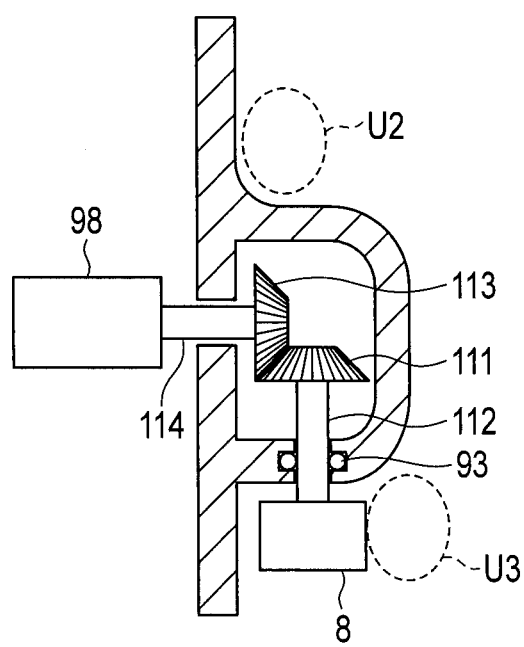
F I G. 18

INTRODUCING APPARATUS

CROSS-REFERENCE TO RELATED APPLICATIONS

This is a Continuation Application of PCT Application No. PCT/JP2014/066351, filed Jun. 19, 2014, which was published under PCT Article 21(2) in Japanese.

This application is based upon and claims the benefit of priority from prior the Japanese Patent Application No.2013-142539, filed Jul. 8,2013 the entire contents of which are incorporated herein by reference.

BACKGROUND OF THE INVENTION

1. Field of the Invention

The present invention relates to an introducing apparatus that allows a bending section to perform an electric bending operation by an operation element provided in an operating section.

2. Description of the Related Art

In general, there is an introducing apparatus including an inserting section that is inserted into a body cavity or a pipeline having bent portions, is flexible and elongated, and has a freely bendable distal end portion. As a typical example, an endoscope apparatus is known which is used for visual observations in the medical field or the industrial field. This endoscope apparatus has an inserting section in which a bending section is continuously provided from a distal end portion where a camera (an observation window) or the like is arranged, and for example, in case of a medical endoscope apparatus, the bending portion is operated by the operating section and inserted into a body cavity while bending in up and down directions and left and right directions.

In recent years, an endoscope apparatus that performs a bending operation with electromotion has been suggested, and a small dial switch is arranged in an operating section of an endoscope main body in place of a manual knob and set so that a bending amount (a bending angle) corresponding to a rotation amount (a rotation angle) can be realized. For example, in an endoscope apparatus suggested in Patent Literature 1: International Publication No. WO2102/074013A1, an RL dial to perform a bending operation with electromotion in RL directions (Right/Left) is arranged under an operating section. It has been suggested that this RL dial is operated to rotate by a middle finger or the like of a hand gripping the operating section. Further, the middle finger of the operator is also used as a holder to prevent a UD knob from unnecessarily rotating.

BRIEF SUMMARY OF THE INVENTION

According to an embodiment of the present invention, there is provided an introducing apparatus comprising: a bending section provided on a distal end side of an inserting section which is inserted into a lumen; an electric bending drive mechanism having an electric drive source to bend the bending section; a rotary knob which instructs the electric bending drive mechanism to perform a bending operation so that the bending section bends in a first direction orthogonal to an inserting direction thereof; an operation element comprising: a dial which instructs the electric bending drive mechanism to perform a bending operation so that the bending section bends in a second direction orthogonal to both the inserting direction and the first direction and which is exposed to the outside; a rotary mechanism which holds the dial to be rotatable on a rotary shaft; a transmission mechanism which transmits a rotation amount of the dial along an axis direction deviating from an axis of the rotary shaft; and a detecting section which outputs an output value according to the rotation amount transmitted by the transmission mechanism; and an operating section which has a rectangular housing and accommodates the operation element therein in such a manner that the rotary knob is arranged on a front surface thereof, a proximal end portion of the inserting section is arranged on a bottom surface continuous from the front surface, a hollow protruding portion is formed on a side surface continuous from the front surface to protrude at a position closer to the proximal end portion of the inserting section than a rotation center position of the rotary knob as seen from the bottom surface, the rotary mechanism alone is arranged in the hollow of the protruding portion, and the detecting section is arranged in the housing.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 17 is a view showing a configuration of a modification of the operation element mounted in the operating section according to the seventh embodiment; and FIG. 18 is a view showing a conceptual appearance configuration of an operation element mounted in an operating section according to an eighth embodiment.

DETAILED DESCRIPTION OF THE PREFERRED EMBODIMENT

Embodiments according to the present invention will now be described hereinafter in detail with reference to the drawings.

[First Embodiment]

Figure 1A:
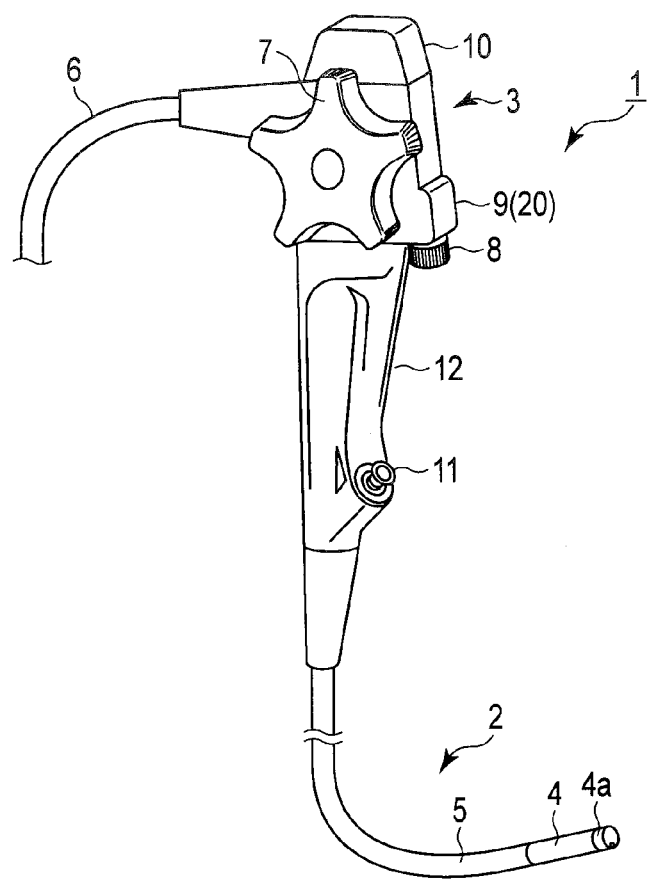
FIG. 1A is a view showing an appearance configuration of an introducing apparatus according to a first embodiment of the present invention.
Figure 1B:
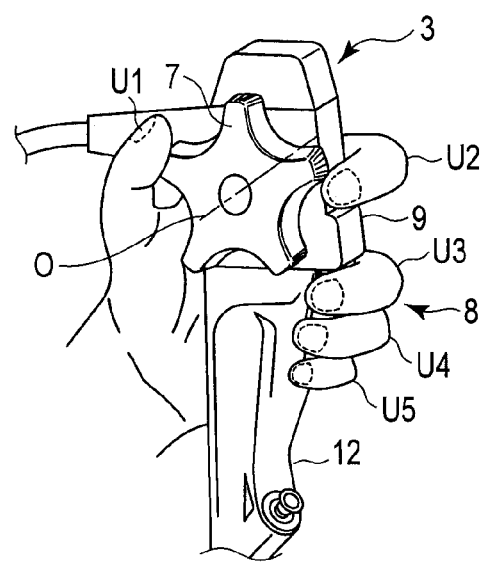
FIG. 1B is a view showing a state that an operating section is gripped by one hand.
Figure 2:
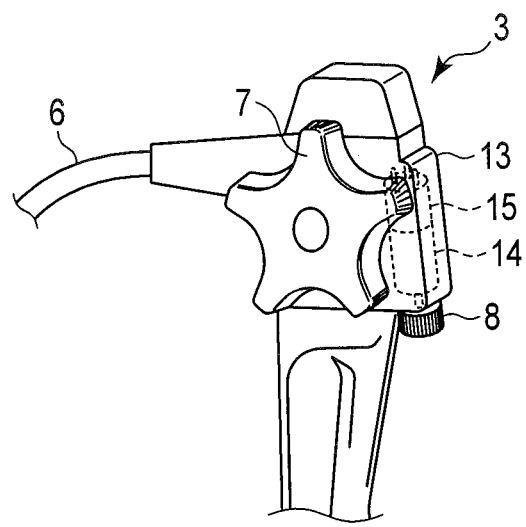
FIG. 2 is a view showing a conceptual appearance configuration of a conventional operating section having an operation part mounted therein for comparison with a first embodiment.

FIG. 1A is a view showing an appearance configuration of an introducing apparatus according to a first embodiment, and FIG. 1B is a view showing a state that an operating section is gripped by one hand. FIG. 2 is a view showing a conceptual appearance configuration of a conventional operating section having a operation part mounted therein for comparison with the first embodiment. The introducing apparatus according to this embodiment is applied to a medical endoscope apparatus whose observation target is the inside of a pore or the inside of a body cavity of a biological body and an industrial endoscope apparatus that observes an inner state of, e.g., a piping or an engine.

An introducing apparatus 1 according to this embodiment, i.e., an endoscope apparatus roughly has an inserting section 2 that is inserted into a body cavity from a distal end side, an operating section 3 coupled with a proximal end side of the inserting section 2, and a universal cord 6 including a light guide, a signal cable, and others extended from the operating section 3.

The inserting section 2 is constituted of a flexible tube section 5 that has flexibility to softly bend, a bending section 4 that is bent in up and down (UD) directions and right and left (RL) directions to an inserting section, a distal end section 4a which is provided at a distal end of the bending section 4 and has a non-illustrated observation window, an illumination window, a forceps window, and others provided therein.

The operating section 3 includes a grip section 12 connected to the inserting section 2, and is constituted of a UD knob (a rotary knob) 7 that bends the bending section 4 in the UD (Up/Down) directions, an RL (Right/Left) dial 8 that bends the bending section 4 in the RL directions, an operation element 17 that is arranged in the later-described operating section 3 including the RL dial 8, and an electric bending drive mechanism 10 that is accommodated in an upper portion of the operating section 3 and includes a motor (not shown) that is an electric drive source.

The bending section 4 is arranged on the distal end side of the inserting section 2, and metallic node rings are sequentially coupled in a direction of a longitudinal axis (a longitudinal axis direction) therein so that they become continuous in a radial direction while being displaced 90 degrees. The bending section is a bending mechanism in which two joints are formed at opposed positions between the node rings and the node rings are rotatably and substantially coaxially coupled. Usually, the bending mechanism is water-tightly covered with a sheet-like member having flexibility. At least two angle wires are coupled with each node ring of the bending mechanism, and a bending operation is performed by towing the respective angle wires so that bending is effected between the joints. When the electric bending drive mechanism 10 tows these angle wires by an actuator such as a motor, the bending operation is performed in the RL directions between the joints. A towing level is adjusted so that a desired bending angle can be formed with an operation amount of the RL dial 8. The bending section 4 and the electric bending drive mechanism 10 constitute a bending function section.

An insertion opening (a forceps opening) 11 from which a pair of forceps, an operation instrument, or the like is inserted is provided in the grip section 12. As will be described later, a part of the operation element 17 is arranged in a hollow (a hollow portion) protruding portion 9 formed in such a manner that the RL dial is exposed to the outside and an exterior surface (an outer surface) protrudes to the outside from a housing of the operating section 3, and a remaining part of the same is arranged in the housing. Further, in this embodiment as well as embodiments and modifications described hereinafter, the RL dial 8 is assumed to be a multi-rotation element that can perform multiple rotations (360 degrees or more)

In a shape example of the operating section 3 according to this embodiment, the housing in which operation members are arranged has a rectangular shape, and the grip section 12 having a tapered shape is integrally disposed on a bottom portion of the housing. The flexible tube section 5 of the inserting section is provided to extend from a tip of a lower portion of the grip section 12.

In the following description of the operating section 3, it is assumed that a surface where the UD knob 7 is arranged is a front surface and a surface on the opposite side, i.e., a surface on which a palm abuts is a back surface. Furthermore, besides the front surface and the back surface of the operating section 3, it is also assumed that a surface from which the universal cable 6 is extended is a first side surface and a surface where the operation element 9 is arranged is a second side surface. Moreover, a surface of the grip section 12 to which a proximal end of the inserting section 2 is disposed is assumed to be a bottom surface of the operating section (or a proximal end side). The opposite side of the bottom surface of the operating section 3 is assumed to be a top surface (or an upper portion). In this embodiment, the motor and others are accommodated in the operating section 3 on the upper surface side.

As shown in FIG. 1B, in this embodiment, as an arrangement of fingers of a hand gripping the operating section 3, a thumb U1 is placed on a protruding portion of a star-shaped UD knob 7 on a first rotary axis from the first side surface via the front surface. Additionally, an index finger U2 wrapping around the back surface reaches the second side surface so that a switch such as a non-illustrated water supply button can be operated.

Further, the index finger U2 can be also placed on the protruding portion of the UD knob 7 on the opposite side of the thumb U1. Furthermore, a middle finger U3 is placed at a position where the protruding portion 9 of the operating section 3 is sandwiched between itself (a lower side) and the index finger (an upper side), and a fingertip is put on the RL dial 8 so that a rotating operation can be performed. A ring finger U4 and a little finger U5 are put on and hold the grip section 12 so that the operating section 3 can be stably gripped. In this embodiment, for a stable UD bending operation, the protruding portions of the UD knob 7 can be assisted by the thumb U1 as well as the index finger U2.

It is to be noted that, although not shown, if the introducing apparatus is an endoscope apparatus, as a publicly known system, the introducing apparatus has an image processing section that executes image processing to an acquired video signal, a universal light source section that emits illumination light, a control unit that executes overall control including each drive control over later-described constituent parts provided in an imaging section or an operating section, a motor drive power supply section that supplies electric power to drive the electric drive mechanism 10, a monitor that displays an observation image subjected to the image processing, and an input device such as a keyboard to configure a setting or make a choice as a matter of course.

FIG. 2 is a view showing an operating section having a publicly known conventional configuration presented for comparison with this embodiment, and shows an appearance shape of the operating section having a rotary mechanism section 14 and an operation element 13 both having cylindrical shapes accommodated in the operating section. The operation element 13 is formed into a cylindrical shape in which an RL dial 8 exposed to the outside, the rotary mechanism section 14, and a potentiometer 15 are linearly coupled. In the operating section shown in the drawing, the additionally provided operation element 13 has a diameter increased without changing its shape.

The operation element to indicate an electric bending amount according to this embodiment will now be described.

Figure 3:
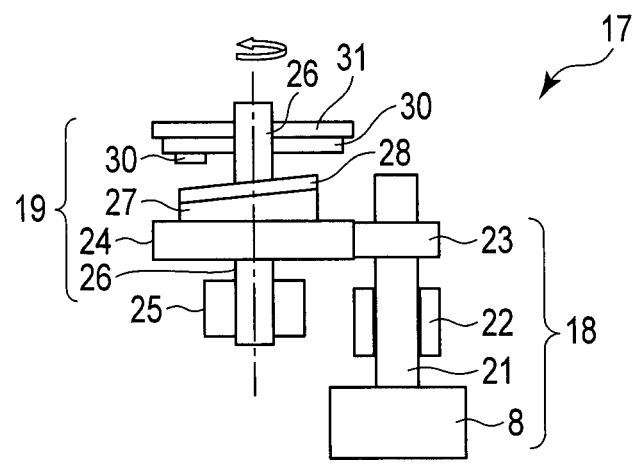
FIG. 3 is a view showing a structural example of an operation element configured to indicate an electric bending amount according to the first embodiment.
Figure 4:
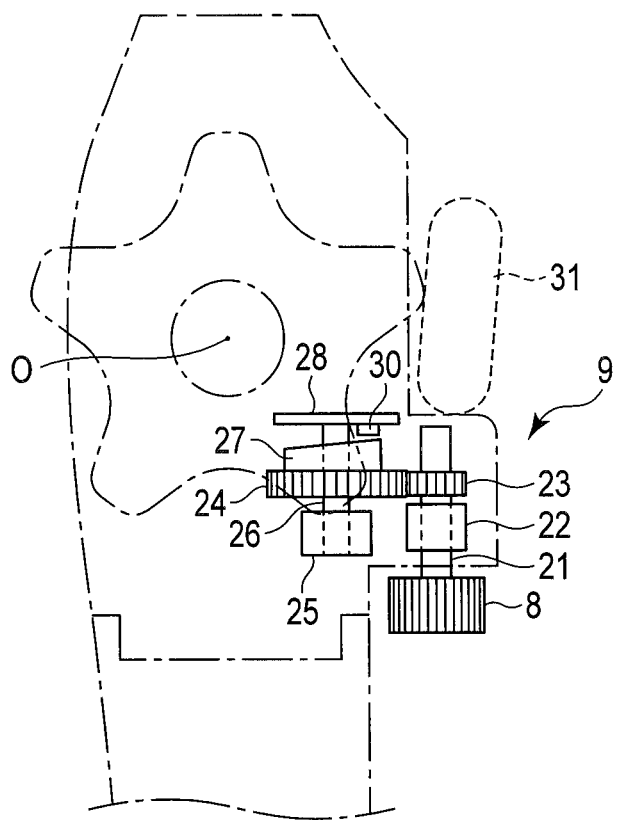
FIG. 4 is a view showing an arrangement example of the operation element according to the first embodiment mounted in the operating section of the introducing apparatus.
Figure 5A:
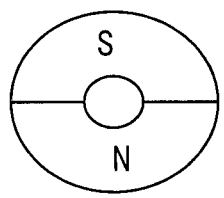
FIG. 5A is a view showing a configuration of a magnetization pattern formed on a magnet of the operation element according to the first embodiment.
Figure 5B:
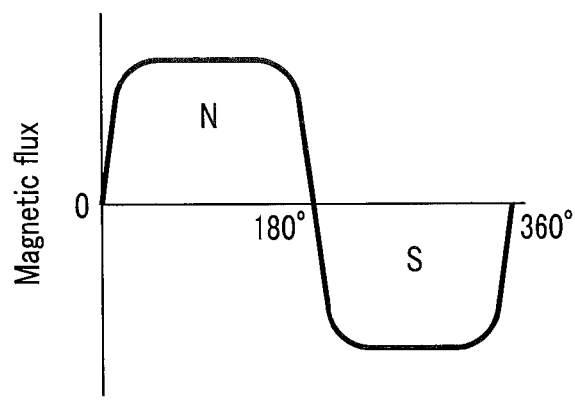
FIG. 5B is a view showing an example of a magnetic flux distribution in the magnetization pattern.
Figure 6A:
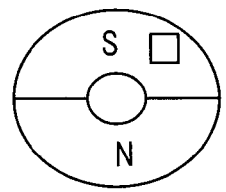
FIG. 6A is a view showing a positional relationship between a magnet plate and a hole element.
Figure 6B:
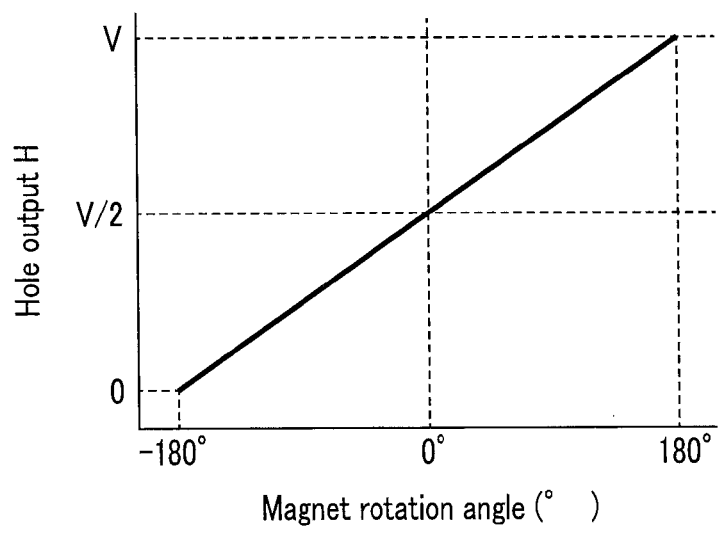
FIG. 6B is a view showing output characteristics of the hole element to a rotation angle of a magnet in the magnetization pattern shown in FIGS. 5.
Figure 7:
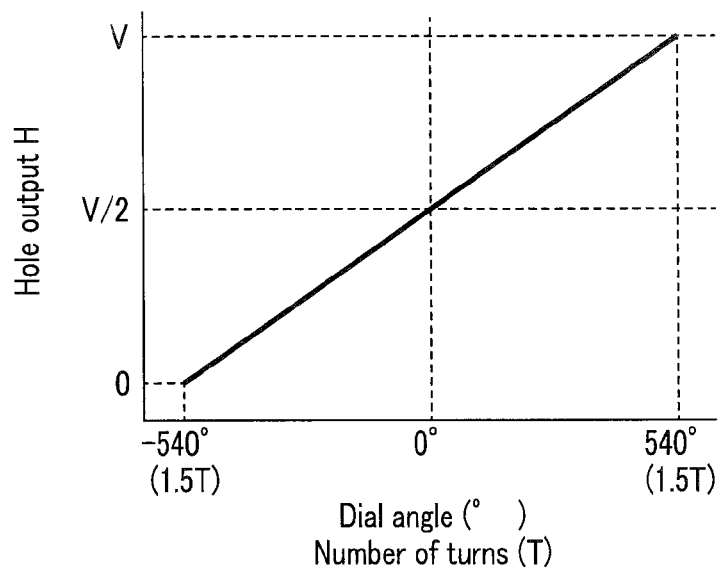
FIG. 7 is a view showing output characteristics of the hole element to a rotation angle of an RL dial in the magnetization pattern shown in FIGS. 5.

FIG. 3 is a view showing a structural example of the operation element 17, and FIG. 4 is a view showing an arrangement example of the operation element 17 mounted in the operating section 3 of the introducing apparatus 1. FIG. 5A is a view showing a configuration of a magnetization pattern formed on a magnet plate of the operation element, and FIG. 5B is a view showing an example of a magnetic flux distribution in the magnetization pattern. Furthermore, FIG. 6 is a view showing output characteristics of a hole element to a rotation angle of the magnet plate to the magnetization pattern, and FIG. 7 is a view showing output characteristics of the hole element to a rotation angle of the RL dial 8 to the magnetization pattern. The example described hereinafter is an example applied to the operation element that bends the bending section in the RL directions.

The operation element 17 according to this embodiment roughly has a rotary mechanism 18 and a hole element detecting section 19, and has a configuration that these members are coupled through a pair of gears 23 and 24 serving as a transmission mechanism that transmits rotating force between them. In this embodiment, although a pair of gears 23 and 24 are an example of the transmission mechanism, the transmission mechanism may be constituted of two or more gears. For example, in case of taking a high gear ratio (a rotation ratio of the RL dial 8 and a driven shaft 26), three or more gears may be combined and configured.

The hold element detecting section 19 according to this embodiment is a detecting section that outputs an output value (a voltage value) according to a rotation amount (or a rotation angle) of the RL dial 8 like a later-described potentiometer. The detecting section, i.e., the hole element detecting section 19 functions as a sensor that outputs a rotation angle in the form of a voltage value. It is to be noted that, in the following description, a neutral position return mechanism of the RL dial 8 additionally provided to the operation element 17 is omitted. Basically, it is a mechanism that returns a position of the RL dial 8 to its original position with the use of energizing force generated in a spring at the time of rotation of a shaft by connecting one end of the spring to a later-described rotary shaft or a driven shaft and connecting the other end to the fixed member.

The rotary mechanism 18 has the RL dial 8 which is at least partly exposed to the outside and rotated by a finger of an operator, a rotary shaft 21 (a second rotary shaft) erected on the RL dial 8 (a rotator), and a bearing section 22 that guides rotation of the rotary shaft 21, and the gear 23 is fitted on a distal end side of the rotary shaft 21. The gear 23 and the gear 24 mesh with each other.

The hole element detecting section 19 has a driven shaft 26 (a third rotary shaft) on which the gear 24 is fitted, a bearing section 25 that guides rotation of the driven shaft 26, a bearer 27 that is arranged on the gear 24 and has an inclined upper surface, a magnet plate 28 arranged along the inclination of this upper surface, a substrate 30 that faces the magnet plate 28 on the driven shaft 26 at an interval on a horizontal plane (horizontally to the inclined surface), a hole element 29 arranged on the substrate 30 on a side facing the magnet plate 28 (the front surface side), and a york 31 integrally bonded to the back surface side of the substrate 30. Magnetic properties of the magnet plate 28 may be either isotropy or anisotropy.

Moreover, the substrate 30 and the york 31 are fixed to a frame of the operation element 17 (not shown) or an inner wall or the like of the operating section 3 by a non-illustrated support member, and configured to rotatably receive the rotary shaft 26. Additionally, although not shown, a watertight member such as an O-ring provided in the housing of the operating section 3 is fitted on the rotary shaft 21. Thus, the operating section 3 is water-tightly configured to prevent a liquid or the like from entering the inside from the outside through the rotary shaft 21.

In this example, the magnet plate 28 is set to make one revolution to three revolutions of the RL dial 8 by setting a gear ratio to the gear 23:the gear 24=1:3. That is, since the number of revolutions from end to end is three, in this embodiment, a position corresponding to 1.5 revolution (T) from both the ends is set as a neutral position, and the bending section is substantially straightened when the RL dial 8 is at the neutral position. Further, the later-described neutral return mechanism is a mechanism that returns the RL dial to the neutral position. It is to be noted that this gear ratio is just an example and can be appropriately changed based on design specifications.

A magnetization pattern having respective semicircles using NS poles shown in FIG. 5A is formed on the magnet plate 8. A waveform of a magnetic flux in this magnetization pattern is such a substantially trapezoidal amplitude shape with rounded edges as shown in FIG. 5B.

In this operation element 17, when the RL dial 8 is rotated, the rotation is transmitted from the gear 23 to the gear 24 through the rotary shaft 21, and the driven shaft 26 rotates. With the rotation of the driven shaft 26, the magnet plate 28 rotates. At this time, as shown in FIG. 6A, the hole element 29 is placed above the inclined magnet plate 28, and its distance to the rotating magnet plate 28 changes to become shorter or longer. The hole element 29 outputs a hole output (V) that linearly changes to such a rotation angle (a rotational position) of the magnet plate 8 as shown in FIG. 6B based on a change in magnetic force (magnetic flux density) due to this change in distance. Further, the hole output to the RL dial 8 causes three revolutions to one revolution of the magnetic plate 8, a dial rotation angle (the number of turns: T) is an angle that is three times a rotation angle of an axis of abscissa in FIG. 6B, and output characteristics of the hole output (V) linearly change in the same manner.

As described above, according to the operation element 17 of the first embodiment, the rotary shaft of the rotary mechanism 18 and the hole element detecting section 19 which is one shaft in conventional examples is formed into two shafts that are coupled through the gears and aligned in the horizontal direction. Consequently, constituent parts continuously arranged in a height direction can be divided in accordance with the height direction and a crossing direction, e.g., the horizontal direction so that they can be slid and arranged. Thus, a part of the operation element 17 (here, the hole element detecting section 19) is moved into the housing of the operating section 3, and the rotary mechanism 18 alone is accommodated in the protruding portion 9 bulging outward from the operating section 3, thus suppressing the protruding portion 9 to a minimum size.

In particular, as shown in FIG. 1B, the protruding portion 9 is arranged at a height position realized by moving the protruding portion 9 to the inserting section 2 side apart from a rotation center position of a rotation axis (a rotation axis O shown in each of FIG. 4 and FIG. 9: a first rotation axis) of the UD knob 7. Consequently, since the protruding portion 9 is provided under the index finger U2 (between this finger and the middle finger), the operation element for electric operations can be incorporated in the operating section without obstructing an operation of the index finger U2 to assist the UD knob 7, thus realizing the introducing apparatus having the operating section 3 with the excellent operability. Moreover, since the operation element is incorporated in the operating section without increasing a diameter (a width and a thickness) to a portion of the operating section on which the index finger is substantially put, no burden is imposed on an operator who can scarcely operate the conventional operating section in a single-handed manner, and the introducing apparatus having the operating section with the excellent operability can be provided.

[Second Embodiment]

Figure 8:
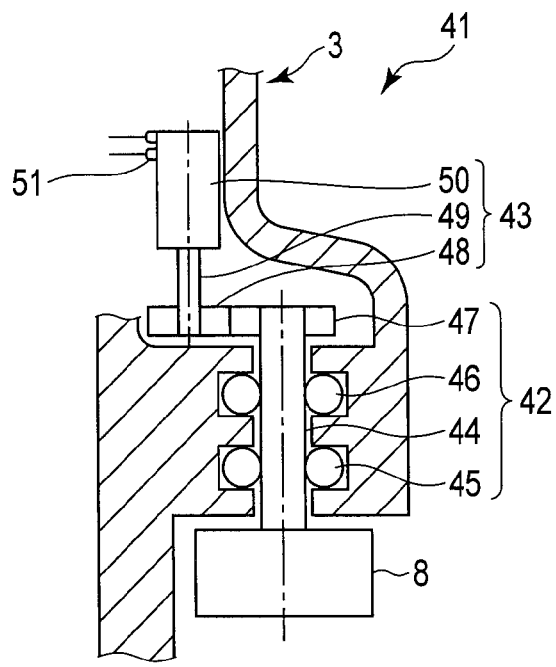
FIG. 8 is a view showing a structural example of an operation element mounted in an operating section of an introducing apparatus according to a second embodiment.

An operation element mounted in an operating section of an introducing apparatus according to a second embodiment will now be described. FIG. 8 is a view showing a structural example of an operation element according to this embodiment. This embodiment has a configuration that a potentiometer 50 is incorporated in place of the hole element detecting section 19. It is to be noted that, in this embodiment, an operation element of an operating section alone will be described, but this embodiment has a configuration equivalent to the introducing apparatus depicted in FIG. 1.

An operation element 41 according to this embodiment is constituted of a rotary mechanism 42 having the same configuration as that described above and a potentiometer section 42, and these members are coupled through a pair of gears 47 and 48 serving as a transmission mechanism that transmits rotational force between them. The potentiometer 50 is a detecting section that outputs an output value (a voltage value) according to a rotation amount (or a rotation angle) of an RL dial 8 like the hole element detecting section 19.

The rotary mechanism 42 has the RL dial 8 that is rotated, a rotary shaft 44 erected on the RL dial 8, O-rings 45 and 46 that are fitted on the rotary shaft 44 and have a watertight function and a shaft rotation guide function, and the gear 47 provided on a distal end side of a rotary shaft 21.

The potentiometer section 42 has a gear 48 meshing with the gear 47, a driven shaft (a potentiometer shaft) 49 fixed through the gear 48, and the potentiometer 50. An output terminal 51 is provided to the potentiometer 50.

In this embodiment, the pair of gears 47 and 48 are adopted as the transmission mechanism of the rotational force, but various configurations can be applied in place of this mechanism.

As, a first example, discoid magnets may be disposed as tips of the shafts respectively, and they may be provided so that circumferential side surfaces of these columnar magnets can abut on each other. As shown in FIG. 5A, the columnar magnet is magnetized so that a semicircular portion has an N pole and a remaining semicircular portion has an S pole. This configuration enables the rotational force to be transmitted to the driven shaft 49 from the rotary shaft 44 in an adsorbed state realized by magnetic force. Additionally, the magnet may have a columnar shape without being restricted to the discoid shape. Further, when truncated circular truncated cone shape magnets are combined to adjust an angle of each conical surface, the rotary shaft 44 and the driven shaft 49 can cross each other not only in the horizontal direction but at a desired angle. Thus, if the rotary mechanism 42 and the potentiometer section 42 cannot be arranged to become parallel or to be aligned due to a restriction of an arrangement space in the operating section 3, they may be arranged at arbitrary angles.

As a second example, when a ring-shaped or discoid roller made of an elastic member, e.g., a rubber material is disposed and arranged at a distal end portion of each shaft so that their circumferential side surfaces are pressed against each other, the rotational force can be transmitted without displacement due to a function of gripping force. These transmission mechanisms can be likewise applied to the first embodiment. A rotation ratio of each shaft can be adjusted by changing a roller outer diameter.

As a third example, like the above-described rollers, magnet rings fitted on the rotary shaft 44 and the driven shaft 49 respectively are used. These magnet rings are configured to have the same specification that N and S poles having the same length are alternately arranged at equal intervals. These magnet rings are fitted and fixed on the respective shafts, and the magnet rings are arranged so that the circumferential side surfaces abut on each other at the same height or arranged at a very small interval so that adsorption force can act. When the magnet ring of the rotary shaft 44 is rotated, the magnet ring on the driven shat 49 side is also synchronously driven and rotated by the adsorption force. The rotation of the rotary shaft 44 is transmitted to the driven shaft 49 by such synchronous rotation.

As described above, according to this embodiment, the same functions and effects as those of the first embodiment can be provided. Moreover, according to this embodiment, the generally distributed potentiometer can be adopted in place of the hole element detecting section 19, the number of components can be reduced, and processes of assembling, adjustment, and component inspection can be simplified.

[Third Embodiment]

Figure 9:
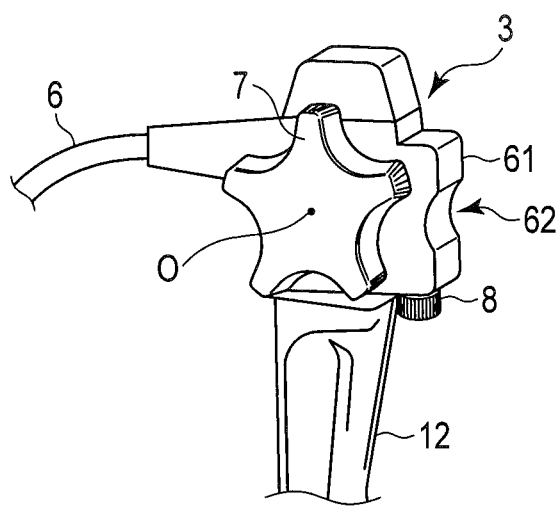
FIG. 9 is a view showing a conceptual appearance configuration of an operation element mounted in an operating section according to a third embodiment.
Figure 10:
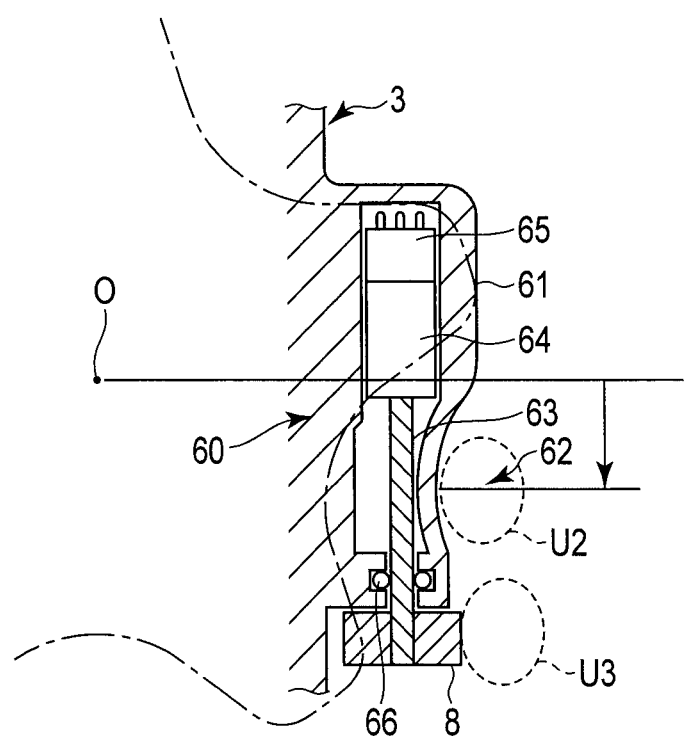
FIG. 10 is a view showing a structural example of the operation element according to the third embodiment.

An operation element mounted in an operating section of an introducing apparatus according to a third embodiment will now be described. FIG. 9 is a view showing a conceptual appearance configuration of an operation element according to this embodiment, and FIG. 10 is a view showing a structural example of the operation element. The operation element 60 according to this embodiment has an appearance shape that a portion on which an index finger is placed is depressed into a curved shape. It is to be noted that, in this embodiment, the operation element of the operating section alone will be described, but the same configuration as the introducing apparatus shown in FIG. 1 is provided in this embodiment, and an inserting section 2, a bending section 4, and others are included.

The operation element mounted in the operating section 3 is configured to have an RL dial 8 that is rotated, a rotary shaft 63 erected on the RL dial 8, an O-ring 66 that is fitted on the rotary shaft 63 and has a water-tight function, a rotary mechanism 64 including the rotary shaft 63, and a potentiometer 65 integrally coupled with the rotary mechanism 64. The operation element 63 is arranged so that constituent parts become continuous on one axis of the rotary shaft 63. On a protruding portion 61, a depressed portion 62 provided by depressing a portion that covers the rotary shaft 63 into a curved shape is formed.

In this embodiment, as shown in FIG. 9 and FIG. 10, a UD knob 7 is arranged on a front side of the operating section 3. The depressed portion 62 has the most deeply curved dent at a position on the protruding portion 61 translated from a rotation center position O of the UD knob 7 (a rotary knob) toward a side surface and at a position moved to an inserting section 2 side (an arrow in FIG. 10). This deepest dent portion is formed so that a fingertip of an index finger U2 placed on the protruding portion 61 can reach a protruding portion (a star-shaped protruding portion) of the UD knob 7 and a middle finger U3 can easily reach the RL dial section 8.

As described above, according to this embodiment, the same functions and effects as those of the first embodiment can be provided. According to this embodiment, since the protruding portion 61 is formed so that the center of the dent of the depressed portion 62 having the curved shape is placed at a position' (close to the inserting section) slightly lower than the rotation center position O of the UD knob 7, the position on which the index finger U2 is placed is preferable, and the middle finger U3 can easily put on the RL dial section 8, thus readily assuring an operation range.

Figure 11A:
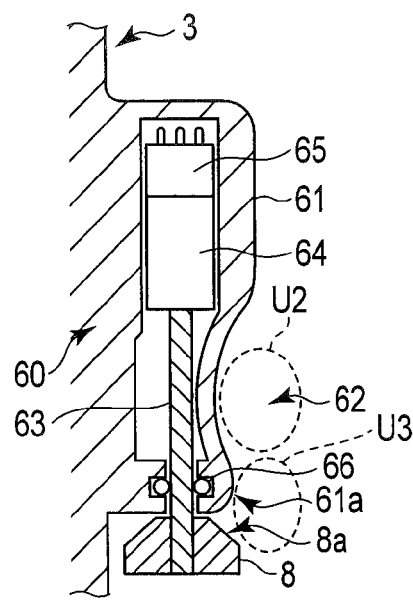
FIG. 11A is a view showing a configuration of a first modification of the operation element according to the third embodiment.

A first modification of the operation element according to the third embodiment will now be described with reference to FIG. 11A. In this modification, like reference numerals denote parts equal to constituent parts in the third embodiment to omit a description thereof.

In the first modification, at a position where the RL dial section 8 faces the protruding portion 61, an angular portion of the RL dial section 8 is subjected to slant chamfering processing 8a, and an angular portion of the protruding portion 61 is subjected to curving processing 61a of scraping away while leaving roundness. These kinds of processing can produce a second dent between the RL dial section 8 and the protruding portion 61.

As described above, according to the first modification, the same functions and effects as those of the first embodiment can be provided. Further, according to the first modification, the fingertip of the middle finger U3 can enter the second dent, the finger can be instinctively put on the RL dial section 8 without visual confirmation and easily hooked on the RL dial section 8, thereby improving the operability.

Figure 11B:
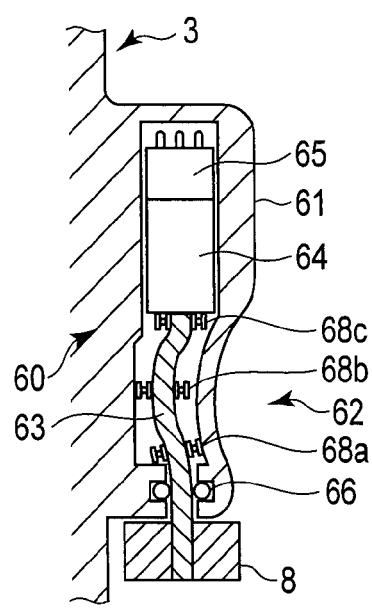
FIG. 11B is a view showing a configuration of a second modification of the operation element.

A second modification of the operation element according to the third embodiment will now be described with reference to FIG. 11B. In this modification, like reference numerals denote parts equal to the constituent parts in the third embodiment to omit a description thereof.

In the third embodiment, since the RL dial 8 is coupled with the rotary mechanism 64 through the rotary shaft 63 made of the linear steel material or the like, the curved shape (the depth of curvature) of the depressed portion 62 is limited. In this modification, a rotary shaft 63 is formed of a wire or the like having flexibility (elasticity). Further, to avoid flexure caused by a rotating operation of the rotary shaft 63, ball bearings 68 (68a, 68b, and 68c) are fitted along the way to thereby allow bending, but rotational force can be transmitted without any loss like the rotary shaft made of the linear steel material. In this modification, the ball bearings are arranged at three positions, i.e., positions near an RF dial 8 and a rotary mechanism 64 and the most curved position to avoid contact with an inner wall surface of a protruding portion 61. Such an arrangement is not restricted, and the number and the arrangement positions of the bearings are appropriately set in accordance with design specifications.

As described above, according to the second modification, the same functions and effects as those of the first embodiment can be provided. Furthermore, according to the second modification, the curvature of the depressed portion 62 of the protruding portion 61 in the operating section 3 can be deepened to realize a curved state which is beyond the linear rotary shaft 63. Moreover, since the bearings 68 are used for fixation, the rotational force of the RL dial 8 can be transmitted to the rotary mechanism 64 with less transmission loss.

Figure 12:
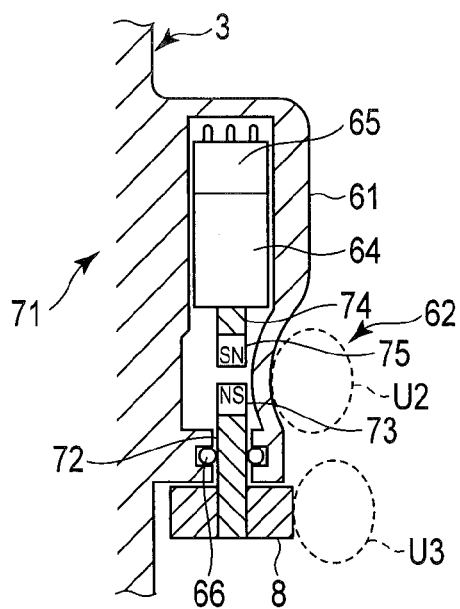
FIG. 12 is a view showing a configuration of a first modification of the operation element according to the third embodiment.

A third modification of the operation element according to the third embodiment will now be described with reference to FIG. 12. In this modification, like reference numerals denote parts equal to the constituent parts in the third embodiment to omit a description thereof.

In the third embodiment, the rotary shaft 63 is made of a linear steel material. In this modification, columnar magnets 73 and 75 are disposed at tips of rotary shafts 72 and 74 disconnected from each other, respectively. In each of the columnar magnets 73 and 75, like the magnetization pattern shown in FIG. 5A, an N pole of a semicircle and an S pole of a remaining semicircle are formed. The different poles (N, S) are arranged to face each other at an interval in the range where magnetic fields act, and attracting magnetic forces act due to mutual magnetic attractions.

In this configuration, when the rotary shaft 72 is rotated by an RL dial 8, the columnar magnet 73 rotates in a state that attracting force of the columnar magnet 73 acts on the columnar magnet 75, and hence the columnar magnet 75 on a driven shaft 74 side is also synchronously driven to rotate. This rotation enables transmitting rotation of the rotary shaft 72 to the drive shaft 74.

As described above, according to the third modification, the same functions and effects as those of the first embodiment can be provided.

[Fourth Embodiment]

An operation element mounted in an operating section of an introducing apparatus according to a fourth embodiment will now be described.

Figure 13:
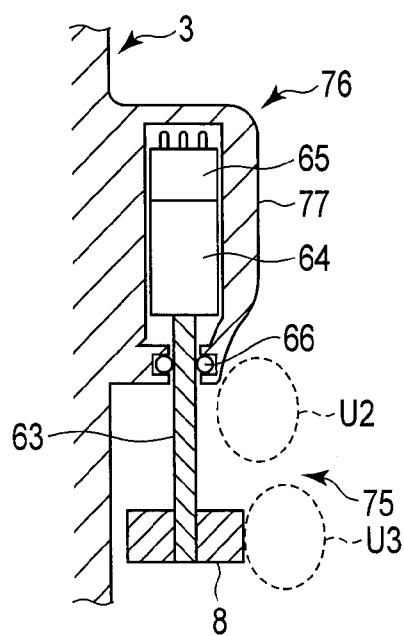
FIG. 13 is a view showing a conceptual appearance configuration of an operation element mounted in an operating section according to a fourth embodiment.

FIG. 13 is a view showing a conceptual appearance configuration of an operation element 76 mounted in an operating section. It is to be noted that, in this embodiment, like reference numerals denote parts equal to the constituent parts in the third embodiment to omit a description thereof. Moreover, in this embodiment, although the operation element in the operating section alone will be described, this embodiment likewise provides the same configuration as the introducing apparatus shown in FIG. 1.

In the operation element 76 according to this embodiment, a protruding portion 77 is shorter than the protruding portion 61 depicted in FIG. 10, and has a shape that is cut off from a lower half part of the curved depressed portion 62. Thus, the protruding portion 77 is substantially arranged at a height position provided by translating from a rotation axis (a rotation center position) O of a UD knob 7 to a side surface. That is, a lower side of the protruding portion 77 is cut off, and a portion of a rotary shaft 63 exposed to the outside is long. This exposed portion of the rotary shaft 63 serves a depressed portion 75 and functions as a space in which an index finger U2 and a middle finger U3 are placed. Additionally, this depressed portion 75 is also formed on a side lower than the rotation center position O of the UD knob 7.

According to this embodiment, in addition to the effects of the first embodiment, since it is possible to reach the rotary shaft 63 and thereby get closer to the operating section 3 as compared with the protruding portion 61, the depressed portion 75 having a wider range can be provided, and an operation range of the middle finger U3 can be easily assured.

[Fifth Embodiment]

Figure 14:
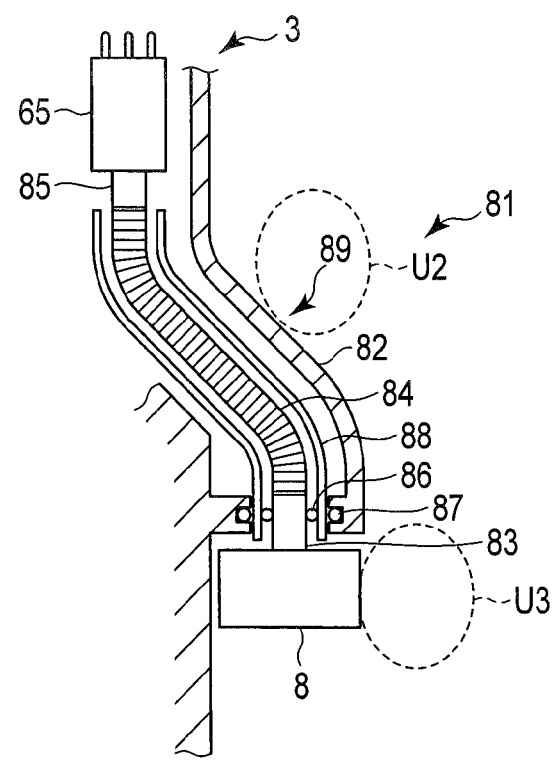
FIG. 14 is a view showing a conceptual appearance configuration of an operation element mounted in an operating section according to a fifth embodiment.

An operation element mounted in an operating section of an introducing apparatus according to a fifth embodiment will now be described. FIG. 14 is a view showing a conceptual appearance configuration of an operation element 81. It is to be noted that the operation element in the operating section alone will be described in this embodiment, but this embodiment likewise provides the same configuration as the introducing apparatus shown in FIG. 1.

The operation element 81 according to this embodiment is accommodated in a protruding portion 82 of an operating section 3, and configured to couple an RL dial 8 with a potentiometer 65 through a bendable flexible shaft 84.

The operation element 81 is constituted of an RL dial 8, a rigid shaft 73 erected on the RL dial 8, a bendable flexible shaft 84 having one end connected to the rigid shaft 73, a rigid shaft 85 connected with the other end of the flexible shaft 84, and a potentiometer 65 connected with the rigid shaft 85. The flexible shaft 84 is wholly accommodated in a tubular sheath 88 having flexibility.

An O-ring 86 fitted on the rigid shaft 73 is arranged between the rigid shaft 73 and the sheath 88, an O-ring 87 fitted in a groove of a protruding portion 82 is arranged between the sheath 88 and the protruding portion 82, and these members are water-tightly configured to prevent a liquid from entering the operating section 3 from respective abutting portions. The flexible shaft 84 extends in the protruding portion 82 from the RL dial 8 exposed to the outside while bending, enters a housing of the operating section 3, and is coupled with the potentiometer 65. The flexible shaft 84 and the rigid shaft 73 are bonded to each other by, e.g., insertion and welding or an adhesion.

With such a configuration, even if the operating section 3 has the configuration in which an arrangement space of the operation element 81 cannot be assured in a rotation axis direction of the RL dial 8 or at a position adjacent to the same, the potentiometer 65 can be appropriately arranged by drawing the flexible shaft 84 around in the housing as long as the flexible shaft 84 can bend.

As described above, according to the operation element 81 of this embodiment, in addition to the effects of the first embodiment, bending of the flexible shaft 84 enables not only assuring a space where an index finger U2 is placed to avoid obstacles to the operability but also arranging the potentiometer 65 by drawing the flexible shaft 84 around in the housing as long as it can bend, which can greatly contribute to a degree of freedom of design.

[Sixth Embodiment]

Figure 15A:
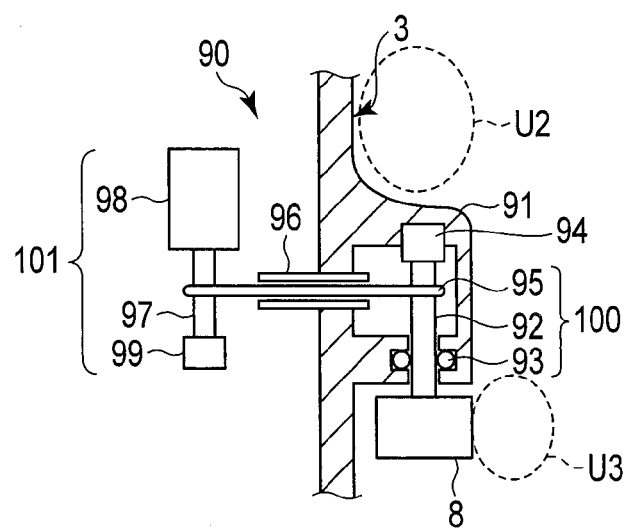
FIG. 15A is a view showing a conceptual appearance configuration of an operation element mounted in an operating section according to a sixth embodiment.
Figure 15B:
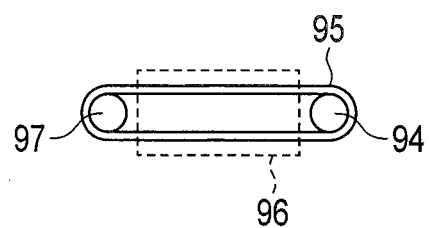
FIG. 15B is a view showing a coupling configuration.

An operation element mounted in an operating section of an introducing apparatus according to a sixth embodiment will now be described. FIG. 15A is a view showing a conceptual appearance configuration of an operation element mounted in an operating section according to the sixth embodiment, and FIG. 15B is a view showing a coupling configuration. It is to be noted that, in this embodiment, the operation element of the operating section alone will be described, but this embodiment provides the same configuration as the introducing apparatus shown in FIG. 1.

An operation element 90 according to this embodiment is roughly constituted of a rotary mechanism 100 and a potentiometer section 101, and these members are coupled by an annular belt 95 that serves as a transmission mechanism that transmits rotational force between them.

As shown in FIG. 15A, the rotary mechanism 100 is accommodated in a protruding portion 91 of an operating section 3, and constituted of an RL dial 8 that is exposed to the outside and rotated by a finger of an operator, a rotary shaft 92 erected on the RL dial 8, and a bearing section 94 that is arranged at a tip of the rotary shaft 92 and guides rotation. The rotary shaft 92 is water-tightly configured to prevent a liquid from entering the inside of the operating section 3 through the rotary shaft 91 by an O-ring 93 fitted in a groove formed near an opening portion of the protruding portion 91. The potentiometer section 101 has a driven shaft (a potentiometer shaft) 97, a potentiometer 98, and a bearing section 99 that is arranged at a tip of the rotary shaft 92 and guides rotation.

Furthermore, as shown in FIG. 15B, an annular belt 95 covered with a sheath 96 is linearly stretched with tension between the rotary shaft 92 and the driven shaft 97. In addition, it is preferable to form a U groove or the like on each of the rotary shaft 92 and the drive shaft 97 so that the belt 95 cannot be displaced from a predetermined position. This belt 95 is used as a transmission mechanism that transmits rotation of the rotary shaft 92 to the drive shaft 97. Thus, it is preferable to create the belt by using a grippy material such as rubber. In addition, in case of setting a rotation ratio of the rotary shaft 92 and the drive shaft 97 described with reference to FIG. 8, shaft diameters may be changed, but a pulley having a diameter that realizes the rotation ratio may be additionally disposed.

Besides, as the belt 95, a V groove may be formed on each of the rotary shaft 92 an the drive shaft 97, and a V belt may be used. Moreover, a timing pulley having a diameter meeting a preset rotation ratio (equal to an output shown in FIG. 8) of each shaft may be fixed, and a toothed belt, which is a so-called timing belt, may be adopted as the belt 95. Additionally, a combination of the gear and the chain may be applied.

As described above, according to the operation element 90 of the sixth embodiment, in addition to the effects of the first embodiment, the simple configuration can realize the present invention.

[Seventh Embodiment]

Figure 16:
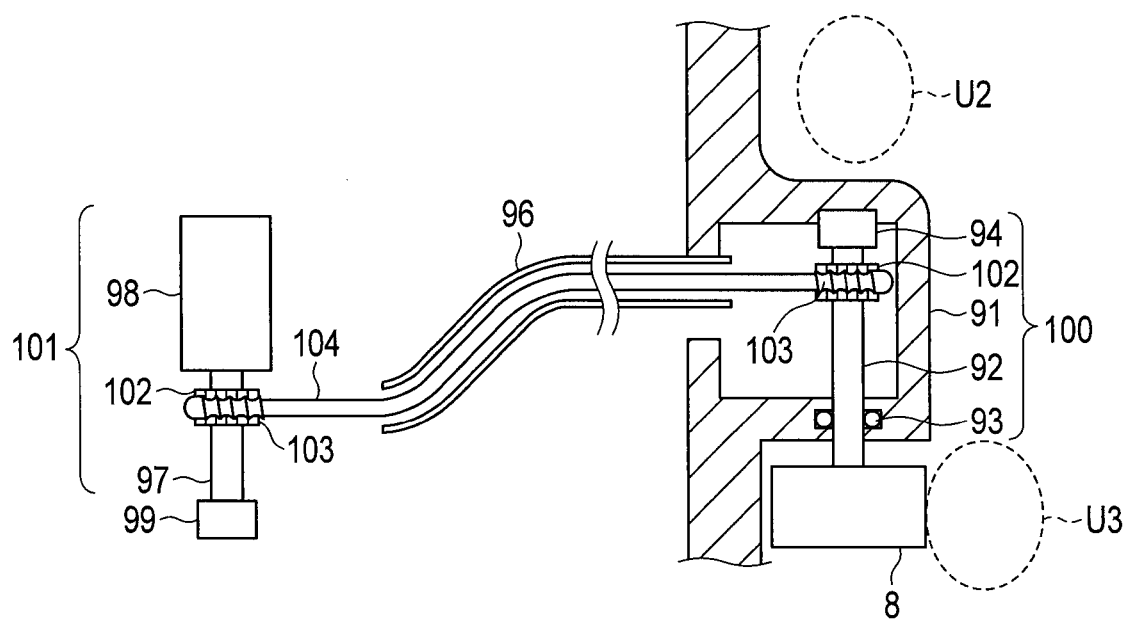
FIG. 16 is a view showing a conceptual appearance configuration of an operation element mounted in an operating section according to a seventh embodiment.

An operation element mounted in an operating section of an introducing apparatus according to a seventh embodiment will now be described. FIG. 16 is a view showing a conceptual appearance configuration of an operation element according to this embodiment. In this embodiment, like reference numerals denote parts equal to the constituent parts in the sixth embodiment to omit a description thereof. It is to be noted that, in this embodiment, the operation element of the operating section alone will be described, but this embodiment provides the same configuration as the introducing apparatus shown in FIG. 1.

Since the transmission mechanism using the belt according to the sixth embodiment applies the tension to transmit the rotational force, the rotary shaft 92 and the driven shaft 97 must be arranged at the positions that are parallel and relatively close to each other, but embodying this configuration may be difficult depending on an arrangement of other constituent parts in the operating section. In this embodiment, since a gear 100 and a screw 101 are combined, the rotary shaft 92 and the driven shaft 97 do not have to be parallel to each other, and they can be arranged at positions apart from each other.

As shown in FIG. 16, an operation element 90 is roughly constituted of a rotary mechanism 100 and a potentiometer section 101. The rotary mechanism 100 is accommodated in a protruding portion 91 of an operating section 3, and constituted of an RL dial 8 that is exposed to the outside and rotated by a finger of an operator, a rotary shaft 92 erected on the RL dial 8, a bearing section 94 that is arranged at a tip of the rotary shaft 92 and guides rotation, a gear 102 fitted on the rotary shaft 92, a screw 103 that meshes with the gear 102, and a wire 104 connected to the screw 103. The rotary shaft 92 is water-tightly configured to prevent a liquid from entering the inside of the operating section 3 through the rotary shat 92 by an O-ring 93 fitted in a groove formed near an opening portion of the protruding portion 91.

Further, a potentiometer section 42 has a potentiometer 98, a driven shaft (a potentiometer shaft) 97 extended from the potentiometer 98, a bearing section 99 that is arranged at a tip of the driven shaft 97 and guides rotation, a gear 102 fitted on the drive shaft 97, and a screw 103 that is provided at an end portion of the wire 104 and meshes with the gear 102. The wire 104 is covered with a sheath 96 from the inside of the protruding portion 91 to a position near the potentiometer 98. When a meshing state of the gear 102 and the screw 103 is held, since the wire 104 has flexibility, the potentiometer section 42 can be arranged at any position and along any direction (as long as the wire 104 can be drawn around) in the operating section 3 if an arrangement space is present.

As described above, according to the operation element of this embodiment, in addition to the effect of the first embodiment, since the wire 104 has the flexibility, the potentiometer section 42 can be easily arranged without being restricted to a position or a direction in the operating section 3 if the arrangement space where the wire 104 can be drawn around is present.

A modification of the operation element according to the seventh embodiment will now be described.

FIG. 17 is a view showing a configuration of a modification of an operation element according to the seventh embodiment. This modification provides a configuration in which a neutral return mechanism that returns an RL dial 8 to a neutral position (a position of a memory indicated by the RL dial 8 when a bending section is straight) is added a driven shaft (a potentiometer shaft) 97 of the potentiometer 98. It is to be noted that, in this embodiment, the operation element of the operating section alone will be described, but this embodiment provides the same configuration as the introducing apparatus shown in FIG. 1.

The neutral return mechanism according to this modification is constituted of a coil spring 105, and its tip portion is fixed to a driven shaft 97 in a state that one end is fixed to an operating section housing or the like and the other end is wound around the drive shaft 97 for more than one turn.

According to this coil spring 105, when an RL dial 8 is close to a neutral position, energizing force is not generated, the driven shaft 97 rotates with an operation of the RL dial 8, and the coil spring 105 is expanded. This expansion causes generation of the energizing force to return the RL dial 8 to its original position.

As described above, according to this modification, since the energizing force generated in accordance with the operation of the RL dial 8 acts as return force to return to the neutral position of the RL dial 8, when a current position (a bent state of a bending section) cannot be recognized when the RL dial 8 is repeatedly rotated more than once, the RL dial 8 can be automatically returned to the neutral position by releasing a hand from it.

[Eighth Embodiment]

An operation element mounted in an operating section of an introducing apparatus according to an eighth embodiment will now be described. FIG. 18 is a view showing a conceptual appearance configuration of an operation element according to this embodiment. This embodiment provides the operation element that adopts a rotational force transmission mechanism using bevel gears. It is to be noted that, in this embodiment, the operation element of the operating section alone will be described, but this embodiment provides the same configuration as the introducing apparatus shown in FIG. 1.

The operation element according to this embodiment has an RL dial 8, a rotary shaft 112 erected on the RL dial 8, a bevel gear 111 provided at a tip of the rotary shaft 112, a potentiometer 98, a bevel gear 113 meshing with the bevel gear 111, and a driven shaft (a potentiometer shaft) 114 extended from the potentiometer 98 connected with the bevel gear 113. A transmission mechanism which is a combination of the bevel gear 111 and the bevel gear 113 converts a rotation axis direction into a crossing direction to effect transmission. An angle of the crossing direction is determined based on angles of tooth flanks of the bevel gears, not necessarily set to a right angle (90°), but appropriately set based on the configuration in the operating section, and may be 90° or more or 90° or less as long as rotation can be smoothly transmitted.

According to the operation element of this embodiment, in addition to the effects of the first embodiment, the invention can be realized with the simple configuration.

[US]Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An introducing apparatus comprising:
a bending section provided on a distal end side of an inserting section which is inserted into a lumen;
an electric bending drive mechanism having an electric drive source to bend the bending section;
a rotary knob which instructs the electric bending drive mechanism to perform a bending operation so that the bending section bends in a first direction orthogonal to an inserting direction thereof;
an operation element comprising: a dial which instructs the electric bending drive mechanism to perform a bending operation so that the bending section bends in a second direction orthogonal to both the inserting direction and the first direction and which is exposed to the outside; a rotary mechanism which holds the dial to be rotatable on a rotary shaft; a transmission mechanism which transmits a rotation amount of the dial along an axis direction deviating from an axis of the rotary shaft; and a detecting section which outputs an output value according to the rotation amount transmitted by the transmission mechanism; and
an operating section which has a rectangular housing and accommodates the operation element therein in such a manner that the rotary knob is arranged on a front surface thereof, a proximal end portion of the inserting section is arranged on a bottom surface continuous from the front surface, a hollow protruding portion is formed on a side surface continuous from the front surface to protrude at a position closer to the proximal end portion of the inserting section than a rotation center position of the rotary knob as seen from the bottom surface, the rotary mechanism alone is arranged in the hollow of the protruding portion, and the detecting section is arranged in the housing.

2. The introducing apparatus according to claim 1, wherein the transmission mechanism is constituted by using any one of gears, an annular belt, a flexible shaft, a pair of magnets, and a wire.

3. The introducing apparatus according to claim 2, wherein the transmission mechanism is constituted of a first gear which is provided at a tip portion of a rotary shaft erected on the dial, and a second gear which is provided at a tip portion of a driven shaft of the detecting section and meshes with the first gear, and transmits rotation of the dial to the operation element.

4. The introducing apparatus according to claim 2, wherein the transmission mechanism is constituted of a first bevel gear which is provided at a tip portion of a rotary shaft erected on the dial, and a second bevel gear which is provided at a tip portion of a driven shaft of the operation element in an axis direction crossing the rotary shaft and meshes with the first bevel gear, and transmits rotation of the dial to the operation element.

5. The introducing apparatus according to claim 1, wherein an edge portion on an outer periphery of the dial around the rotary shaft which faces a housing of the operating section is chamfered.

6. An introducing apparatus comprising:
an inserting section which is inserted into a subject;
a bending section which is provided on a distal end side of the inserting section and which is configured to be inserted into the subject;
a rotary knob which is operable by an operator to bend the bending section in a first direction;
an operation element which is operable by the operator to bend the bending section in a second direction different from the first direction;
a grip section connected to a proximal end portion of the inserting section;
a housing which is connected to a proximal end portion of the grip section, gripped together with the grip section by the operator, and has a front surface on which the rotary knob is arranged and a back surface which is arranged on the opposite side of the front surface and on which a palm of the operator abuts when the operator grips;
a universal cable extending in an extending direction away from a first side surface continuous from the front surface and the back surface of the housing;
a protruding section which is protruded from the housing in an opposite direction of the extending direction of the universal cable, the protruding portion forming a space in which a part of the operation element is accommodated; and
a depressed portion which is depressed in a manner to extend toward an inside of the housing at a position of the protruding portion, the position being at a portion of the protruding portion in which the operation element is accommodated.

7. The introducing apparatus according to claim 6, wherein the depressed portion is formed in such a manner that a center of the depressed portion is arranged at a position closer to the grip section than a rotation center position of the rotary knob.

8. The introducing apparatus according to claim 6, wherein the position of the depressed portion being further at the portion of the protruding portion where the operation portion is not exposed to the operator.

* * * * *